United States Patent [19]

Huber et al.

[11] 4,273,742
[45] Jun. 16, 1981

[54] DRAIN APPARATUS FOR THE REACTION VESSEL IN AN ATOMIC ABSORPTION INSTRUMENT

[75] Inventors: Bernhard Huber; Winfried Gönner, both of Überlingen, Fed. Rep. of Germany

[73] Assignee: Bodenseewerk Perkin-Elmer, Überlingen, Fed. Rep. of Germany

[21] Appl. No.: 78,977

[22] Filed: Sep. 26, 1979

[30] Foreign Application Priority Data

Nov. 25, 1978 [DE] Fed. Rep. of Germany ....... 2851058

[51] Int. Cl.³ ................... G01N 27/66; G01N 21/13; G01N 33/20
[52] U.S. Cl. ..................................... 422/80; 422/81; 422/116; 23/230 A
[58] Field of Search .................................. 422/78–82, 422/112, 113, 116; 23/230 A; 141/130; 137/624.18, 624.2

[56] References Cited

U.S. PATENT DOCUMENTS

| 3,844,719 | 10/1974 | Hammitt | 422/78 |
| 3,929,411 | 12/1975 | Takano et al. | 422/81 |
| 4,121,907 | 10/1978 | Roque | 422/81 |
| 4,230,665 | 10/1980 | Huber | 422/116 |

Primary Examiner—Michael S. Marcus
Attorney, Agent, or Firm—S. A. Giarratana; E. T. Grimes; R. A. Hays

[57] ABSTRACT

Disclosed is a system for the measurement of the atomic absorption of gaseous samples including a reaction vessel and conduits for supplying liquid sample, carrier gas and a reagent to the vessel. A discharge conduit is coupled between the reaction vessel and the measuring cell of an atomic absorption spectrometer. The reaction vessel has a drain conduit and a relief valve in the drain conduit. Control means are provided for controlling the flow of liquid sample, carrier gas, reagent and gaseous sample through the corresponding conduits in accordance with the predetermined program for making consecutive measurements. A pressure sensor is provided for sensing pressure in the reaction vessel above a specified pressure indicative of incomplete draining of the vessel and below a specified pressure indicative of substantially complete draining of the vessel. The control means is coupled to the pressure sensor and is responsive to a pressure above the specified pressure to disable the system from a subsequent measurement.

5 Claims, 4 Drawing Figures

DRAIN APPARATUS FOR THE REACTION VESSEL IN AN ATOMIC ABSORPTION INSTRUMENT

BACKGROUND OF THE INVENTION

The present invention relates generally to apparatus for automatically measuring the atomic absorption of gaseous measuring samples generated consecutively from a series of sample liquids and particularly relates to a drain for the reaction vessel of the measuring system whereby complete draining of the sample from the reaction vessel is ensured before a subsequent measurement can be made.

In co-pending U.S. Pat. Application Ser. No. 917,829 filed June 22, 1978, now U.S. Pat. No. 4,230,665, there is disclosed a device for automatically measuring the atomic absorption of gaseous meauring samples generated consecutively from a series of sample liquids including a reaction vessel connected to a carrier gas source through a carrier gas supply conduit and to a heated measuring cell through a carrier discharge conduit. The cell is located in the optical path of rays of an atomic absorption spectrometer. Reagent is supplied to the reaction vessel through a reagent supply conduit and sample is supplied to the reaction vessel by a sample transport system through a sample supply conduit. The reaction vessel has a drain with a valve at its lower end through which the contents of the reaction vessel are drained to a waste container. In that construction, liquid from the reaction vessel is discharged into the waste container at a predetermined time during the measuring cycle.

SUMMARY OF THE PRESENT INVENTION

It is a primary object of the present invention to provide a novel and improved system for draining a reaction vessel of liquid in an atomic absorption measuring system.

It is another object of the present invention to provide a novel and improved system for draining a reaction vessel in an atomic absportion measuring system wherein consecutive measurements are taken and draining of the reaction vessel is ensured prior to a subsequent measurement cycle.

It is another object of the present invention to provide a novel and improved drain for the reaction vessel in an atomic absorption measuring system wherein the system controller is responsive between measuring cycles to the pressure in the reaction vessel to initiate or preclude the next measuring cycle.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the present invention, as embodied and broadly described herein, a system for measurement of the atomic absorption of gaseous samples in accordance with the present invention comprises a reaction vessel, first, second and third conduits for supplying a liquid sample, a carrier gas, and at least on reagent respectively to the reaction vessel, a discharge conduit coupled between the vessel and the measuring cell of an atomic absorption spectrometer, a valve disposed in the discharge conduit for flowing a gaseous sample from the reaction vessel to the measuring cell when the valve is open and preventing flow of gaseous sample from the reaction vessel to the measuring cell when the valve is closed, control means for controlling the flow of liquid sample, carrier gas, reagent, and gaseous sample through the first, second, third and gaseous discharge conduits, respectively, in accordance with a predetermined program for making consecutive measurements and including means coupled to the valve to closing the valve at the end of the first measurement and opening the valve for a subsequent measurement, means for draining the reaction vessel including a drain conduit and a relief valve in the conduit, a pressure sensor for sensing pressure in the reaction vessel above a specified pressure indicative of incomplete draining of the reaction vessel and below the specified pressure indicative of a substantially complete draining of the reaction vessel, the control means being coupled to the pressure sensor and responsive to the pressure above the specified pressure in the reaction vessel to disable the system from a subsequent measurement.

The invention consists in the novel parts, constructions, arrangements, combinations and improvements shown and described. The accompanying drawings, which are incorporated in and constitute a part of the specification, illustrate one embodiment of the invention and, together with the description, serve to explain the principles of the invention.

DESCRIPTION OF A PREFERRED EMBODIMENT

Reference will now be made in detail to the present preferred embodiment of the invention, an example of which is illustrated in the accompanying drawings.

Figure 1:
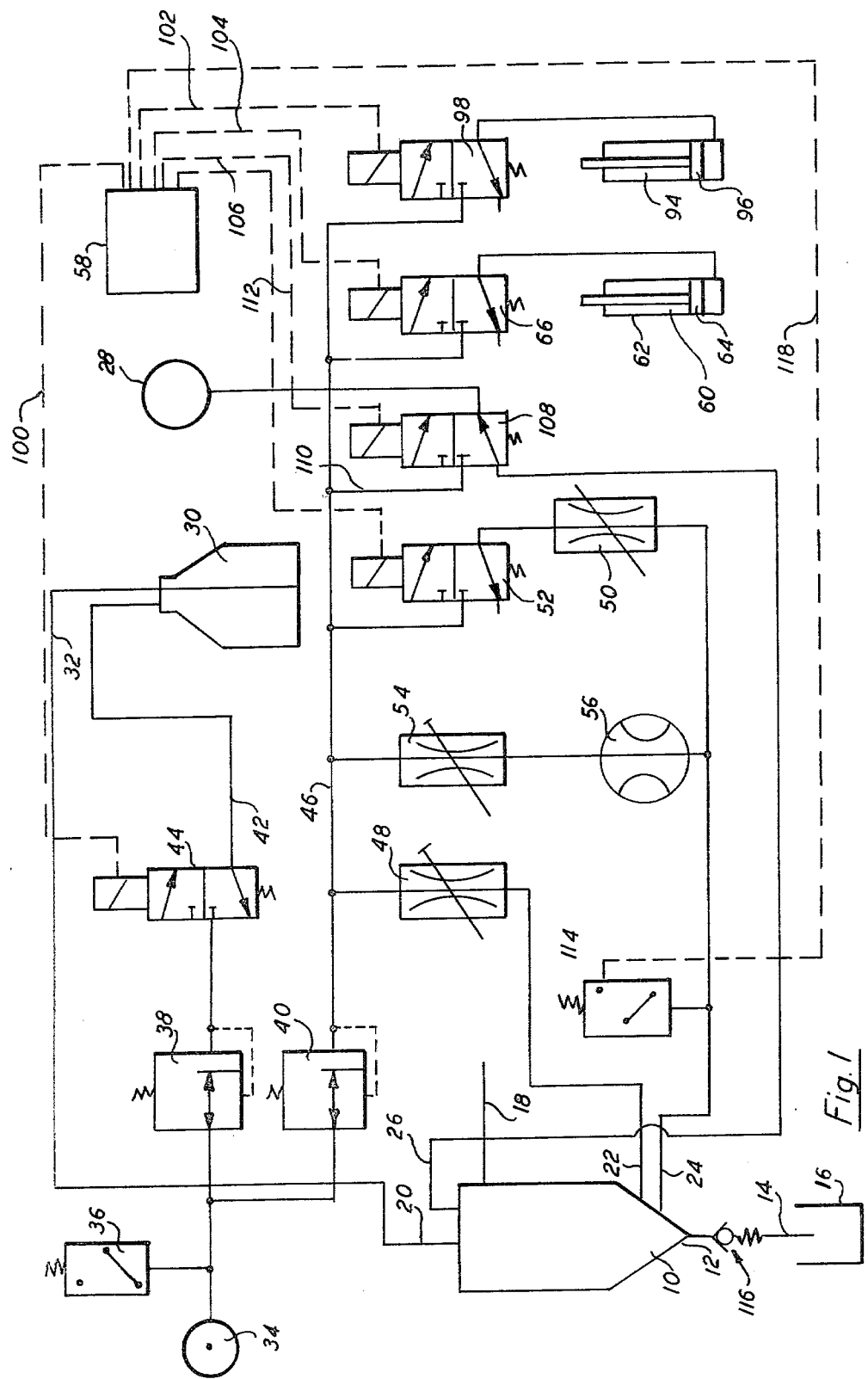
FIG. 1 is a schematic view of a gaseous sample measuring system constructed in accordance with the present invention.

Referring now to the drawings, particularly to FIG. 1, there is illustrated a device for automatically generating and measuring gaseous samples from a series of sample liquids including a reaction vessel designated 10. Reaction vessel 10 comprises a substantially funnel shaped drain 12 from which a drain conduit 14 extends to a waste container 16. A relief valve 116 is disposed in conduit 14 an is biased toward its closed position. A sample conduit 18, a reagent supply conduit 20 and carrier gas supply conduits 22 and 24 open into reaction vessel 10. In the illustrated embodiment, sample supply conduit 18 opens into the upper portion of reaction vessel 10, while the carrier gas supply conduits 22 and 24 open into the lower end of the reaction vessel 10. A connecting conduit 26 extends from the upper end of reaction vessel 10 and opens at its opposite end through a valve 108 into a heatable measuring cell 28. Measuring cell 28 may be heated by suitable known devices. For example, cell 28 may comprise a graphite tube with electrodes at its opposite ends, and which cell is located in the path of rays of an atomic absorption spectrometer, not shown.

Pneumatic means are provided for withdrawing reagent liquid from a closed supply container 30 including a reagent supply conduit 20 connected to conduit 32 which extends through the closure of the supply container 30 to its bottom. A carrier gas source 34 is connected through a pressure responsive switch 36 to the inlets of pressure regulators 38 and 40 respectively connected in parallel. The outlet of first pressure regulator 38 is connected to supply container 30 through a connecting conduit 42, the connecting conduit 42 extending through the closure of supply container 30 and terminating at the top of container 30. The first pressure regulator 38 enables the carrier gas pressure in connecting conduit 42 to be adjusted to a pressure, for example, about 0.15 bar. A solenoid actuated shut-off valve 44 is disposed in connecting conduit 42.

A carrier gas conduit 46 is connected to the outlet of the second pressure regulator 40. The tube carrier gas supply conduits 22 and 24 branch from carrier gas conduit 46 and open into the funnel shaped drain 12 of reaction vessel 10. Carrier gas supply conduit 22 is provided with an adjustable flow restrictor 48. Also, carrier gas supply conduit 24 contains an adjustable flow restrictor 50 and a valve 52. The carrier gas flowing in conduit 46 is adjusted by the second pressure regulator 40 to a pressure, for example, about 1.4 bar.

A controller 58 is coupled to the two solenoid valves 44 and 52 as indicated by the respective dash lines 100 and 106. Valves 44 and 52 are controlled in a push-pull mode, whereby valve 44 is opened only when valve 52 is closed. Thus, pressurized carrier gas is supplied to supply container 30 when carrier gas is supplied to reaction vessel 10 only through the heavily restricted carrier gas supply conduit 22. Consequently, the carrier gas pressure within reaction vessel 10 cannot impede the supply of reagent liquid thereto through connecting conduit 32.

Figure 2:
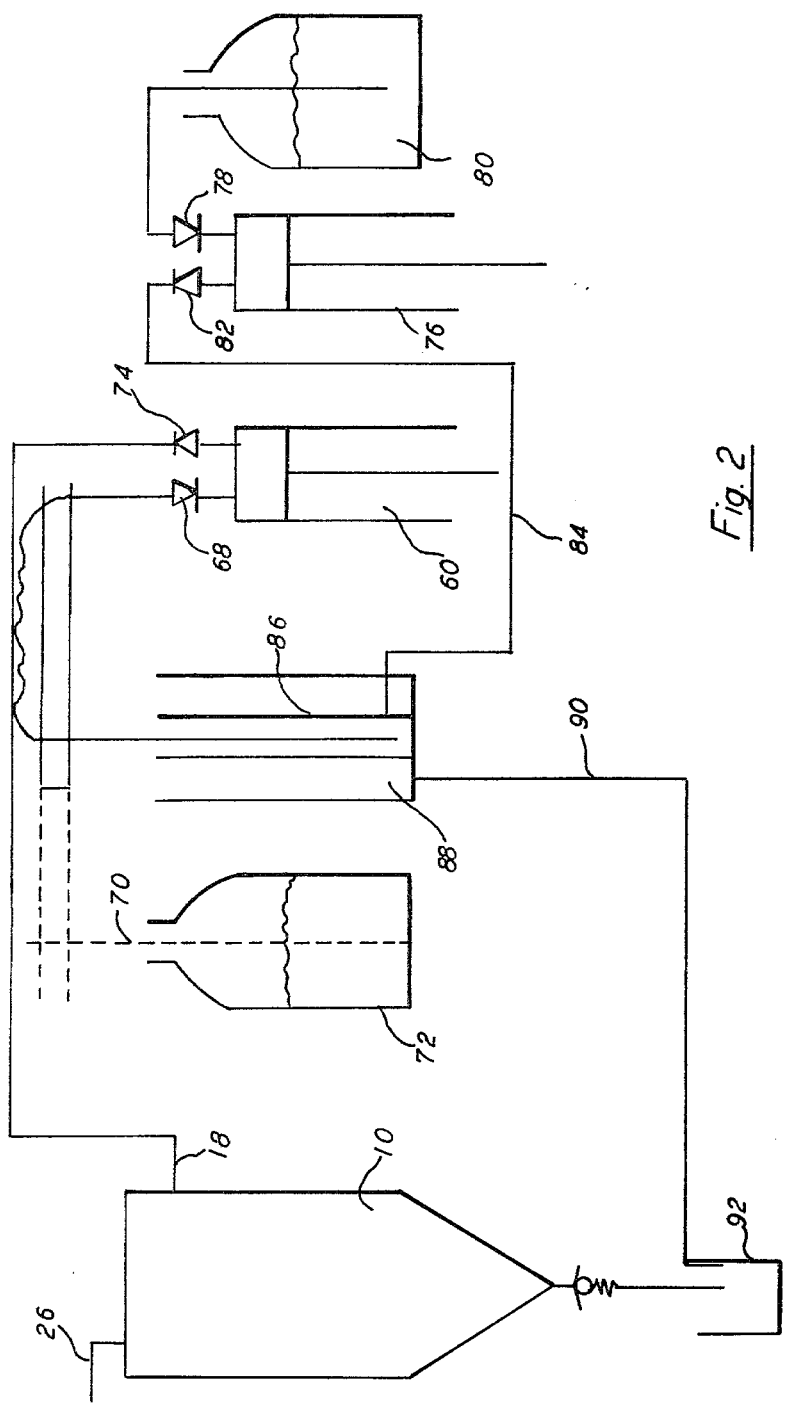
FIG. 2 is a schematic view particularly illustrating the pumps for the sample and flushing liquids utilized in the system of FIG. 1.

A second reagent liquid may be supplied in a corresponding manner as previously described from a second supply container, not illustrated in the drawing figures. Thus, with solenoid actuated valve 44 open and solenoid actuated valve 52 closed, reagent from supply container 30 is fed to reaction vessel 10 through reagent supply conduit 20 with a relatively low carrier gas pressure due to pressure regulator 38. Sample is supplied to sample supply conduit 18 by a sample pump 60 (FIG. 2). Sample pump 60 is arranged for actuation by a pneumatic cylinder 62 (FIG. 1) having a piston 64. Pneumatic cylinder 62 is controlled by the application of carrier gas pressure in carrier gas conduit 46 through a solenoid actuated shut-off valve 66.

As illustrated in FIG. 2, sample pump 60 suctions sample liquid from a sample vessel 72 through a valve 68 and an intake tube 70 when intake tube 70 is in the position illustrated by the dashed lines in FIG. 2. When pump 60 is reversed, sample liquid is discharged through a valve 74 and through the sample supply conduit 18 into reaction vessel 10. Further, a flushing liquid pump 76 is provided which suctions flushing liquid from a flushing liquid container 80 for supply thereof through a valve 82 and a conduit 84 to an overflow vessel 86. The intake tube 70 is movable by suitable machanisms, not shown, between the positions illustrated in FIG. 2, to dip into the sample vessel 72 and into the overflow vessel 86 filled with flushing liquid.

The sample vessels may be arranged on a turntable. The constructional design of this arrangement may be similar to that disclosed in U.S. Pat. No. 4,111,051 issued Sept. 5, 1978. The overflow 88 of the overflow vessel 86 is connected to a waste container 92 through a conduit 90.

As illustrated in FIG. 1, the flushing liquid pump 76 is actuated by a pneumatic cylinder 94 having an actuator piston 96. Cylinder 94 is connected to carrier gas conduit 46 through a ⅜ directional solenoid actuated control valve 98.

As indicated by dash lines 100, 102, 104, 106, solenoid valves 44, 98, 66, and 52 are controlled by controller or programmer 58. Controller 58 operates to first close valve 52 and open valve 44. Reagent is thus fed through conduit 20 to reagent vessel 10 at a constant flow rate. In the position of valve 66 illustrated in FIG. 1, the lower chamber of pneumatic cylinder 62 is vented.

Thus, sample pump 60 makes an intake stroke and suctions sample liquid from sample vessel 72, as illustrated in FIG. 2. After a specified time interval, the solenoid for valve 66 is actuated by controller 58 to shift valve 98 whereby carrier gas is directed into the lower chamber of pneumatic cylinder 62. Piston 64 thus actuates sample pump 60 to discharge the sample liquid suctioned from the sample vessel 72 into reaction vessel 10 through sample supply conduit 18 for mixing with a reagent or reagents. Subsequently, valve 44 is closed and valve 52 is opened whereby carrier gas flows into reaction vessel 10 through carrier gas supply conduit 24 with only minor restrictions and conveys the hydrides or the like from vessel 10 through conduit 26 to measuring cell 28.

At the same time, intake pipe 70 is moved from the sample vessel 72 to the overflow vessel 86, as illustrated by the solid lines in FIG. 2. Overflow vessel 86 is supplied with flushing liquid by a flushing liquid pump 76 in a quantity enabling an exchange of flushing liquid within the overflow vessel whereby cross-contamination is avoided.

Under the control of solenoid actuated valve 66 and actuator piston 64, sample pump 60 makes second intake and discharge strokes respectively suctioning flushing liquid from vessel 86 and feeding the flushing liquid through sample supply conduit 18 to vessel 10, thus cleaning vessel 10 and the connecting conduits.

To drain sample from reaction vessel 10, a ⅜ directional control valve 108 is provided in the carrier gas discharge conduit 26. In the position illustrated in FIG. 1, control valve 108 provides communication between measuring cell 28 and vessel 10 through passage 26. In the other position of valve 108, passage 26 is closed and communication between the carrier gas conduit 46 and the measuring cell 28 through conduit 110 is established. When valve 108 is closed, carrier gas flow is thus established to measuring cell 28. Solenoid valve 108 is controlled by programmer 58, as indicated by the dash line 112.

A pressure sensor 114 is provided in communication with the carrier gas supply conduit 24. Sensor 114 responds to a pressure above a predetermined pressure in the carrier gas supply conduit 24 and thus to pressures in the reaction vessel 10 in excess of the predetermined pressure.

A relief valve 116 opens in a direction to drain vessel 10 through drain conduit 14. Valve 116 is normally biased by a spring into a closed condition preventing reaction vessel 10 from being drained. When open, valve 116 governs the flow passage from the reaction vessel 10 through drain 12 and drain conduit 14 to waste container 16. When valve 108 is closed by programmer 58 after completion of a measurement and communication between the reaction vessel 10 and measuring cell 28 is precluded, the pressure in the reaction vessel 10 will increase. When the predetermined pressure in the reaction vessel 10 is exceeded, pressure sensor 114 provides a signal to programmer 58, as indicated by the dashed line 118. The pressure within vessel 10 continues to increase as long as sample or flushing liquid remains in reaction vessel 10. This liquid experiences a relatively high flow resistance in the drain valve 116 and drain conduit 14 due to its viscosity. When reaction vessel 10 is drained completely, however, only carrier gas will flow through valve 116 into waste containers 16. The flow resistance to carrier gas is, of course, substantially smaller, whereby the carrier gas pressure build-up in reaction vessel 10 breaks down and pressure sensor 114 returns to its normal inactivated state which corresponds to a pressure in the reaction vessel below the predetermined pressure.

Figure 4:
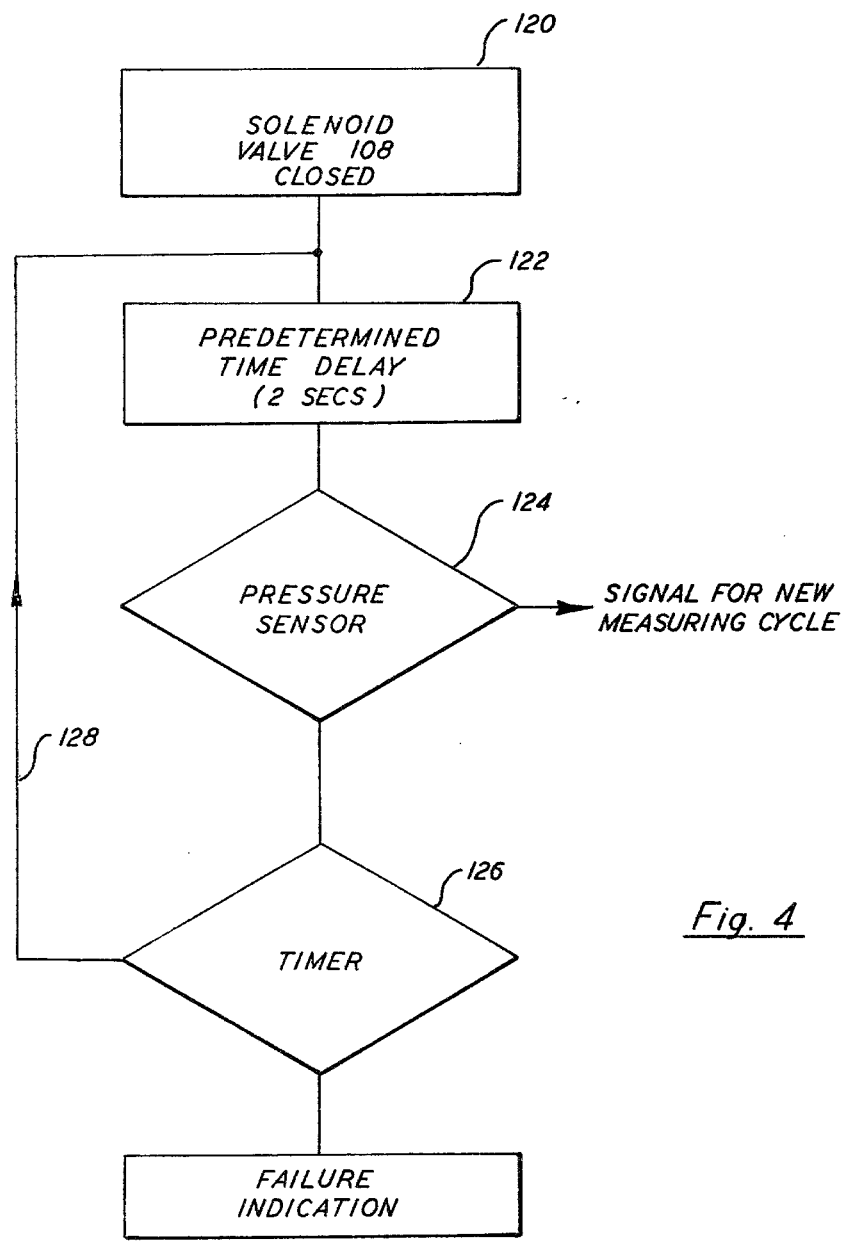
FIG. 4 is a flow diagram of a program for controlling the draining of sample liquid from the reaction vessel.

The control can be affected in the manner illustrated in the flow diagram of FIG. 4. At the end of the measuring procedure, the solenoid valve 108 is closed as indicated by box 120. The box labelled 122 represents a predetermined time delay, for example, two seconds. After this time delay has elapsed, the pressure sensor is either actuated by sensing the pressure in the vessel 10 above the predetermined pressure in which event a signal is transmitted to the programmer, or remains unactuated in which event no signal is transmitted to the programmer. This is illustrated by block labelled 124 in FIG. 4. If the pressure in the reaction vessel is below the predetermined pressure, the pressure sensor 114 remains unactuated after the waiting time of two seconds. This indicates that the sample liquid has drained completely from reaction vessel 10.

The controller is programmed to switch to the next measuring cycle after the predetermined time period has elapsed and no pressure signal is received. With sample remaining in the pressure vessel, however, a pressure build-up takes place in the vessel during the waiting time of two seconds and the programmer is signaled to delay the next measuring cycle.

Thus, if the pressure sensor remains unactuated after the two second delay, the programmer signals the start of a new measuring cycle. If however, the pressure sensor is actuated, indicating the reaction vessel 10 is not yet completely drained, the sensing of the pressure signal by the programmer initiates a new pressure sensing cycle. This is indicated by the line 128 in FIG. 4. The pressure signal transmitted to the programmer, resultant from sensing pressure in the reaction vessel above a predetermined pressure, is also transmitted to a second timer indicated by the block 126 in FIG. 4 such that if the pressure signal is actuated after the two second delay, the testing or pressure sensing cycle is repeated through line 128 at predetermined time intervals. In the event that the pressure signal is deactuated after one or more of the test or pressure sensing cycles has been completed, the programmer will commence a new measuring cycle. However, should the testing continue for thirty seconds with the pressure signal remaining actuated, a failure indication indicated by the box 130 in FIG. 4 is provided and it can be assumed that the sample is not drained from the reaction vessel due, for example, to clogging of the drain. Thus, all subsequent measuring cycles are deferred until the draining problem has been cured.

In the alternative, the programmer can be switched to the measuring cycle if, and only if, the pressure sensor has been actuated and thereafter deactuated. This checks whether a pressure has built up and whether the carrier gas is present with the pressure sensor responding to the build-up. Consequently, once the pressure build-up has deteriorated by the draining of the vessel, the pressure sensor would remain unactuated. In such case, the starting of the program occurs with the first sample, because initially the reaction vessel is empty.

Figure 3:
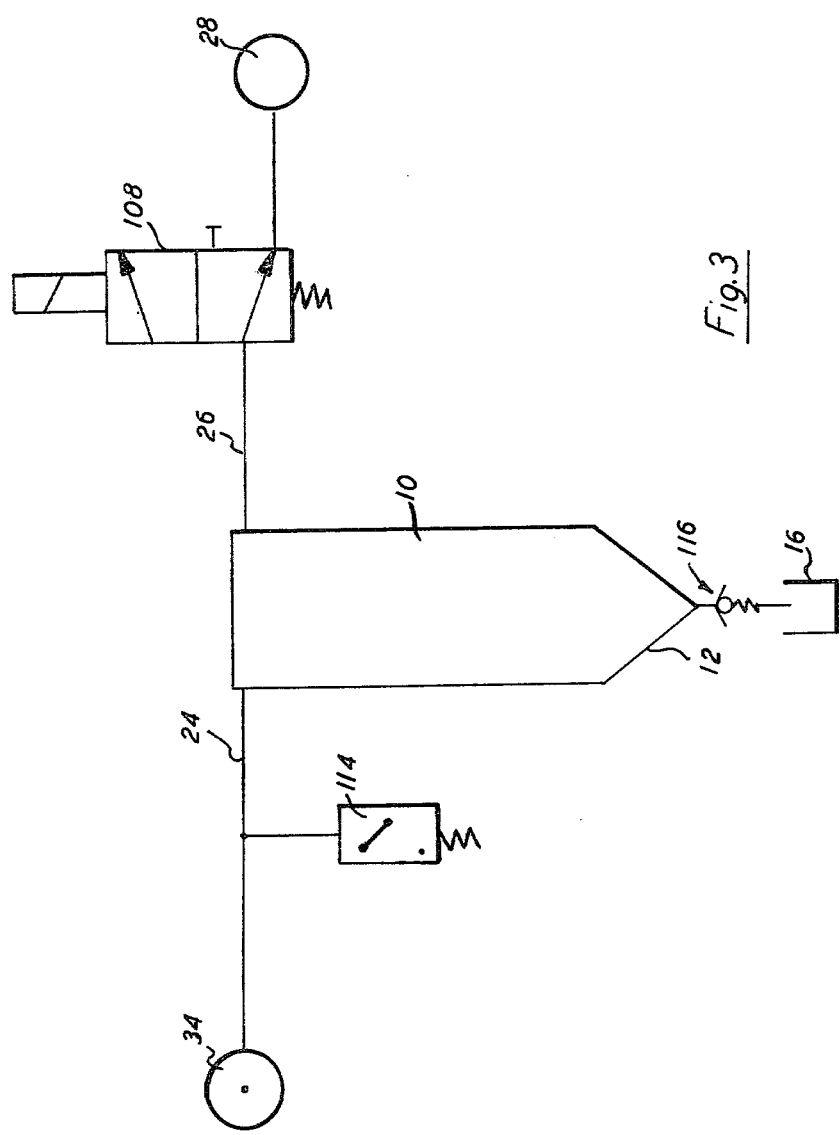
FIG. 3 is a schematic view illustrating the pressure sensor and valve coupled to the reaction vessel for ensuring proper draining of the vessel.

Referring now to FIG. 3, the components essential for the draining reaction action vessel 10 in accordance with the procedures described hereinbefore are illustrated. Particularly, the carrier gas source 34 is connected through conduit 24 to the pressure sensor 114 and to the reaction vessel 10. The carrier gas discharge 26 connects between the vessel 10 through the valve 108 to the measuring cell 28. Adjacent the lower end of vessel 10 is the relief valve 116 for draining the contents of vessel 10 into the refuse container 16. This Figure thus diagramatically illustrates the operation of the draining system.

It will be apparent to those skilled in the art that various modifications and variations can be made in the present invention without departing from the spirit or scope of the invention.

What is claimed is:

1. A system for the measurement of the atomic absorption of gaseous samples comprising:

a reaction vessel, first, second and third conduit means for supplying a liquid sample, a carrier gas, and at least one reagent, respectively, to said reaction vessel, a discharge conduit means coupled between said reaction vessel and a measuring cell of an atomic absorption spectrometer, a valve means disposed in said discharge conduit means for permitting the flow of a gaseous sample from said reaction vessel to said measuring cell when said valve is open and for preventing the flow of said gaseous sample from said reaction vessel to said measuring cell when the valve is closed, control means for controlling the flow of liquid sample, carrier gas, reagent and gaseous sample through said first, second, third and gaseous discharge conduit means, respectively, in accordance with a predetermined program for making consecutive measurements and including means coupled to said valve means for closing said valve means at the end of the first measurement and opening said valve means for a subsequent measurement, means for draining said reaction vessel including a drain conduit means and a relief valve in said conduit means, a pressure sensor in communication with said carrier gas conduit means for sensing pressure in said reaction vessel above a specified pressure indicative of incomplete draining of said reaction vessel and below said specified pressure indicative of a substantially complete draining of said reaction vessel, said control means being coupled to said pressure sensor and responsive to a pressure above said specified pressure in said reaction vessel to disable the system from a subsequent measurement.

2. A system according to claim 1 wherein said control means includes means for providing a failure signal, said failure signal providing means being responsive to pressures in said vessel greater than said specified pressure after a predetermined time period.

3. A system according to claim 1 wherein said control means includes means for providing an enabling signal said enabling signal providing means being responsive, after a specified time delay, to pressures less than said specified pressure in said reaction vessel whereby said system is able to make subsequent measurements.

4. A system according to claim 3 wherein said control means includes means for testing, at periodic intervals, said pressure in said reaction vessel and providing a failure signal responsive to sensing pressures greater than or equal to said specified pressure after a predetermined time period which includes a plurality of said specified time delays.

5. A system according to claim 1 wherein said control means includes means for enabling the next measuring cycle only if said pressure sensor has first indicated a pressure equal to or greater than said specified pressure in said reaction vessel and subsequently a pressure less than said specified pressure in said reaction vessel.

* * * * *